(12) United States Patent
Carangelo

(10) Patent No.: US 9,310,294 B2
(45) Date of Patent: Apr. 12, 2016

(54) USE OF ONE OR MORE RETRO-REFLECTORS IN A GAS ANALYZER SYSTEM

(71) Applicant: MKS Instruments, Inc., Andover, MA (US)

(72) Inventor: Robert M. Carangelo, Glastonbury, CT (US)

(73) Assignee: MKS Instruments, Inc., Andover, MA (US)

( * ) Notice: Subject to any disclaimer, the term of this patent is extended or adjusted under 35 U.S.C. 154(b) by 65 days.

(21) Appl. No.: 14/275,309

(22) Filed: May 12, 2014

(65) Prior Publication Data

US 2015/0160126 A1    Jun. 11, 2015

Related U.S. Application Data

(60) Provisional application No. 61/825,263, filed on May 20, 2013.

(51) Int. Cl.
*G01N 21/3504* (2014.01)
*G01N 21/39* (2006.01)
(Continued)

(52) U.S. Cl.
CPC ............ *G01N 21/3504* (2013.01); *G01N 21/39* (2013.01); *G01N 33/0027* (2013.01); *G01N 2201/068* (2013.01);
(Continued)

(58) Field of Classification Search
CPC .............. G01N 21/3504; G01N 21/39; G01N 21/7746; G01N 2201/06113; H01S 3/105; H01S 5/141

USPC .................................................. 356/432–440
See application file for complete search history.

(56) References Cited

U.S. PATENT DOCUMENTS 5,128,797 A  *  7/1992  Sachse .................... G01N 3/08
                                                          356/370
5,331,409 A  *  7/1994  Thurtell ................ G01N 21/39
                                                          250/345

(Continued)

FOREIGN PATENT DOCUMENTS

| CN | 103076090 A |   | 5/2013 |
| JP | 402028981 A | * | 1/1990 |
| WO | 0204903 A1  |   | 1/2002 |

OTHER PUBLICATIONS (C1) International Search Report from corresponding PCT Patent Application No. PCT/US2014/037870 dated Aug. 13, 2014.
(Continued)

*Primary Examiner* — Hoa Pham
(74) *Attorney, Agent, or Firm* — Proskauer Rose LLP

(57) ABSTRACT

Methods and systems are provided for monitoring at least one gas in a sample gas. An exemplary system includes a source used for generating a beam of radiation, at least one retro-reflector configured to receive the beam of radiation from the source in an incident direction and reflect the beam of radiation toward the source in alignment with the incident direction, and a motor configured to move the at least one retro-reflector with respect to the source in a direction collinear with the incident direction. The system also includes a sample cell storing a sample gas comprising at least one gas. The sample cell is configured to allow at least a portion of an extracted beam of radiation from a cavity, defined by the source and the at least one retro-reflector, to propagate therethrough.

26 Claims, 7 Drawing Sheets

(51) Int. Cl.
  *G01N 33/00* (2006.01)
  *H01S 3/105* (2006.01)
  *H01S 5/00* (2006.01)
  *H01S 5/022* (2006.01)
  *H01S 5/14* (2006.01)
  *H01S 5/34* (2006.01)

(52) U.S. Cl.
  CPC ...... *G01N 2201/06113* (2013.01); *H01S 3/105* (2013.01); *H01S 5/0071* (2013.01); *H01S 5/02248* (2013.01); *H01S 5/141* (2013.01); *H01S 5/3401* (2013.01)

(56) References Cited

U.S. PATENT DOCUMENTS

| | | | |
|---|---|---|---|
| 5,381,010 A * | 1/1995 | Gordon | G01J 1/16 250/339.13 |
| 6,040,914 A * | 3/2000 | Bortz | G01N 3/433 250/345 |
| 6,108,355 A | 8/2000 | Zorabedian | |
| 6,205,159 B1 | 3/2001 | Sesko et al. | |
| 6,339,609 B2 | 1/2002 | Lefevre | |
| 6,556,599 B1 | 4/2003 | Svilans | |
| 7,209,498 B1 | 4/2007 | Chapman et al. | |
| 7,230,960 B2 | 6/2007 | Nguyen et al. | |
| 7,466,734 B1 | 12/2008 | Day et al. | |
| 7,623,234 B2 | 11/2009 | Puzey | |
| 7,894,057 B2 | 2/2011 | Puzey | |
| 8,253,932 B1 | 8/2012 | Cole | |
| 2007/0002922 A1 | 1/2007 | McDonald | |
| 2007/0127539 A1 | 6/2007 | Wang et al. | |
| 2013/0221209 A1* | 8/2013 | Kamba | G01N 21/3581 250/225 |
| 2014/0111808 A1* | 4/2014 | Nikodem | G01N 21/31 356/409 |

OTHER PUBLICATIONS (C2) Sonnenfroh et al., "Observation of CO and CO2 absorption near 1.57 μm with an external-cavity diode laser," Applied Optics, vol. 36 (15), May 20, 1997, pp. 3298-3300.

Notification Concerning Transmittal of Copy of International Preliminary Report on Patentability to corresponding PCT Application No. PCT/US2014/037870 issued Dec. 3, 2015, 10 pages.

* cited by examiner

USE OF ONE OR MORE RETRO-REFLECTORS IN A GAS ANALYZER SYSTEM

CROSS REFERENCE TO RELATED APPLICATION

This application claims the benefit of and priority to U.S. Provisional Patent Application No. 61/825,263, filed May 20, 2013, the entire contents of which is owned by the assignee of the instant application and incorporated herein in its entirety.

FIELD OF THE INVENTION

The invention generally relates to detecting and quantifying one or more gases in a gas sample, and specifically to evaluating gas samples using quantum cascade laser (QCL) modulated by one or more retro-reflectors.

BACKGROUND

A quantum cascade laser (QCL) can be used with an external cavity to detect and/or measure the concentration of one or more specific gases in a gas sample. To perform such detection, a flat mirror can be positioned in the external cavity to reflect an incident beam generated by the QCL back upon itself in a direction aligned with (i.e., parallel to) the direction of the incident beam. In addition, a grating can be used to generate beams of different wavelengths for propagation through the gas sample. Signals resulting from such propagation can be used to measure the concentration of one or more gases in the gas sample.

One disadvantage associated with this arrangement is that it is difficult to align a flat mirror perpendicularly relative to a QCL beam in an external cavity because such a beam is often an invisible, infrared beam. Another disadvantage is that, if a movable flat mirror is used to alter the external cavity length dynamically (e.g., to provide mode hop free wavelength scanning), the motion mechanism used to move the flat mirror needs to maintain the mirror perpendicularly to the incident QCL beam while in motion, which can be a difficult and costly endeavor. Yet another disadvantage is that frequent adjustment of the flat mirror and/or the grating may be needed because beams of different wavelengths originate from different parts of a QCL layered structure. Therefore, a beam originating from the QCL, after propagating through a collimating lens, can be aimed in slightly different directions in the external cavity depending on its wavelength. If no adjustment is made to the flat mirror or the grating, the output beam can fail to lase, change amplitude, mode hop to an unpredictable wavelength, and/or fail to be correctly correlated to the grating tilt angle.

SUMMARY

The present technology simplifies QCL external cavity mirror alignment and facilitates alignment maintenance over a broad range of lasing wavelengths. For example, at least one movable retro-reflector can be used to provide beam alignment as it moves. The motion of the retro-reflector can impose high frequency wavelength modulation of the QCL. In general, by appropriately tuning the QCL and/or the retro-reflector(s), a mode hop free light source is provided that can create beams over a desired range of wavelengths, which are usable for scanning and measuring the concentration of one or more gases in a gas cell. The present technology also provides systems and methods for quantifying the concentration of one or more gases in a gas sample. For example, as a beam of radiation produced by the QCL external cavity propagates through a gas sample containing at least one gas, the concentration of the gas can be determined based on the phase or intensity (i.e., magnitude) measurements of an output signal generated by the sample.

In one aspect, a system for monitoring at least one gas in a sample gas is provided. The system includes a source for generating a beam of radiation, at least one retro-reflector, a motor, a sample cell, a detector and a processor. The at least one retro-reflector is configured to receive the beam of radiation from the source in an incident direction and reflect the beam of radiation toward the source in alignment with the incident direction, thereby causing radiation in a cavity defined by the source and the at least one retro-reflector to obtain a desired wavelength. The motor is configured to move the at least one retro-reflector with respect to the source in a direction collinear with the incident direction. The sample cell stores the sample gas comprising the at least one gas. The sample cell is configured to allow at least a portion of an extracted beam of radiation from the cavity to propagate therethrough. The detector, in optical communication with the sample cell, is configured to generate an output signal at the output of the sample cell based on the extracted beam of radiation propagating through the sample cell. The processor, in electrical communication with the detector, is configured to determine a concentration of the at least one gas in the sample gas based on the output signal received by the detector.

In some embodiments, the processor is further configured to perform at least one of (i) transmit a first signal to a power supply to adjust a current or voltage provided to the source or (ii) transmit a second signal to the motor to move the retro-reflector by a distance. At least one of the first or second signal modulates a wavelength of the radiation in the cavity to obtain the desired wavelength.

In some embodiments, the system further includes a beam splitter located external to the cavity. The beam splitter is configured to split the at least a portion of the extracted beam of radiation into a first beam of radiation and a second beam of radiation. The first beam of radiation is directed through the sample cell. The second beam of radiation is directed through a reference path containing a reference gas. The system further includes a second beam splitter for combining the first beam of radiation and the second beam of radiation to generate a first recombined beam of radiation. The detector, in optical communication with the second beam splitter, is configured to generate a first recombined signal based on the first recombined beam of radiation. The reference gas can be air. The system can also include a second sample cell storing the reference gas, where the second sample cell is positioned along the reference path to allow the second beam of radiation to propagate therethrough. The system can further include one or more additional retro-reflectors located external to the cavity along the reference path to modulate a phase of the first recombined signal by changing a path length of the second beam of radiation.

The detector can additionally generate a second recombined signal based on a second recombined beam of radiation that is produced as a combination of (1) the first beam of radiation after traversing through the reference path and (2) the second beam of radiation after traversing through the sample cell without the sample gas stored therein. In this case, the processor can be configured to determine the concentration of the at least one gas in the sample gas by determining a phase difference between the first and second recombined signals.

In some embodiments, the system further includes a beam splitter located external to the cavity. The beam splitter configured to split the at least a portion of the extracted beam of radiation into first, second, third and fourth beams of radiation. The first and second beams of radiation propagates through a reference path containing a reference gas. The system also includes a first mirror positioned at an input of the sample cell that contains the sample gas. The first mirror is adapted to receive the third beam of radiation and substantially reflect the third beam of radiation toward the beam splitter. The system further includes a second mirror positioned at an output of the sample cell to receive the fourth beam of radiation and substantially reflect the fourth beam of radiation back through the sample cell toward the beam splitter. The first and fourth beams of radiation are adapted to recombine at the beam splitter to generate a first recombined beam. The second and third beams of radiation are adapted to recombine at the beam splitter to generate a second recombined beam.

The system can further include a third mirror adapted to receive (i) the first recombined beam of radiation and transmit the first recombined beam of radiation to a first detector to generate a first recombined signal, and (ii) the second recombined beam of radiation and transmit the second recombined beam of radiation to a second detector to generate a second recombined signal. In this case, the processor can be configured to determine the concentration of the at least one gas in the sample gas by determining a phase difference between the first and second recombined signals.

In another aspect, a method for monitoring at least one gas in a sample gas is provided. The method includes generating a beam of radiation and directing the beam of radiation to at least one retro-reflector along an incident direction within a cavity defined by the source and the at least one retro-reflector. The beam of radiation is reflected by the at least one retro-reflector toward the source in a direction aligned with the incident direction, thereby causing radiation in the cavity to obtain a desired wavelength. The method also includes directing at least a portion of an extracted beam of radiation from the cavity to propagate through a sample cell that stores the sample gas comprising the at least one gas. The method further includes generating an output signal based on the portion of the extracted beam of radiation propagating through the sample cell to determine a concentration of the at least one gas in the sample gas and modulating a wavelength of the radiation in the cavity to obtain the desired wavelength. Modulating the wavelength can include at least one of adjusting a current or voltage for generating the beam of radiation or moving the at least one retro-reflector by a distance collinear to the incident direction.

In some embodiments, the method further includes splitting the extracted beam of radiation into a first beam of radiation and a second beam of radiation, directing the first beam of radiation through the sample cell containing the sample gas, and directing the second beam of radiation through a reference path containing a reference gas. The method also includes recombining the first beam of radiation and the second beam of radiation to generate a first recombined beam of radiation, based on which a first recombined signal is generated.

The method can further include replacing the sample gas in the sample cell with the reference gas, directing the first beam of radiation through the sample cell, and directing the second beam of radiation through the reference path. The first beam of radiation and the second beam of radiation can be combined to generate a second recombined beam of radiation, based on which a second recombined signal is generated.

The method can further include determining the concentration of the at least one gas in the sample gas by detecting a phase difference between the first and second recombined signals. In addition, a phase of the first or second recombined signal can be modulated by changing a path length of the second beam of radiation along the reference path using one or more retro-reflectors.

In some embodiments, the method further includes splitting, by a beam splitter, the extracted beam of radiation into first, second, third and fourth beams of radiation, directing the first and second beams of radiation through a reference path containing a reference gas, and directing the third beam of radiation toward a first mirror positioned at an input of the sample cell. The third beam of radiation is substantially reflected by the first mirror toward the beam splitter. In addition, the fourth beam of radiation is directed through the sample cell toward a second mirror positioned at an output of the sample cell, where the fourth beam of radiation is substantially reflected by the second mirror through the sample cell toward the beam splitter. The method also includes combining the first and fourth beams of radiation at the beam splitter to generate a first recombined beam of radiation and combining the second and third beams of radiation at the beam splitter to generate a second recombined beam of radiation.

The method can further includes receiving, by a third mirror, the first and second recombined beams of radiation, directing, by the third mirror, the first recombined beam of radiation to a first detector to generate a first recombined signal, and directing, by the third mirror, the second recombined beam of radiation to a second detector to generate a second recombined signal. The concentration of the at least one gas in the sample gas can be determined by computing a phase difference between the first and second recombined signals.

In other examples, any of the aspects above can include one or more of the following features. The distance to move the at least one retro-reflector is determined as a function of (1) a wavenumber of the extracted beam of radiation, (2) an amount of wavenumber change desired in the extracted beam of radiation, and (3) a current distance between the source and the retro-reflector.

In some embodiments, at least one silicon-based etalon is located between the source and the retro-reflector in the cavity to confine the radiation in the cavity to within a desire wavelength range.

In some embodiments, a plurality of retro-reflectors are positioned to increase an optical path length gain of the radiation in the cavity, thereby minimizing a distance between the plurality of retro-reflectors and the source by an amount proportional to the optical path length gain. The plurality of retro-reflectors can be configured to receive the beam of radiation from the source and generate a number of reflective beam paths in the cavity collinear to the incident direction. The resulting optical path length gain is proportional to the number of reflective beam paths. The plurality of retro-reflectors can comprise a first retro-reflector and a second retro-reflector with a relationship defined by $d2=d1/n$, where (i) d1 represents a first normal distance between an apex of the first retro-reflector and the beam of radiation, (ii) d2 represents a second normal distance between an apex of the second retro-reflector and the apex of the first retro-reflector, and (iii) n represents the number of reflective beam paths. At least one of the first normal distance (d1) or the second normal distance (d2) can be adjusted to change the number of reflective beam paths (n).

In some embodiments, the concentration of the at least one gas in the sample gas is determined by analyzing the output signal to detect an intensity of absorption by the sample gas of the at least a portion of the extracted beam of radiation.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

DETAILED DESCRIPTION

Figure 1:
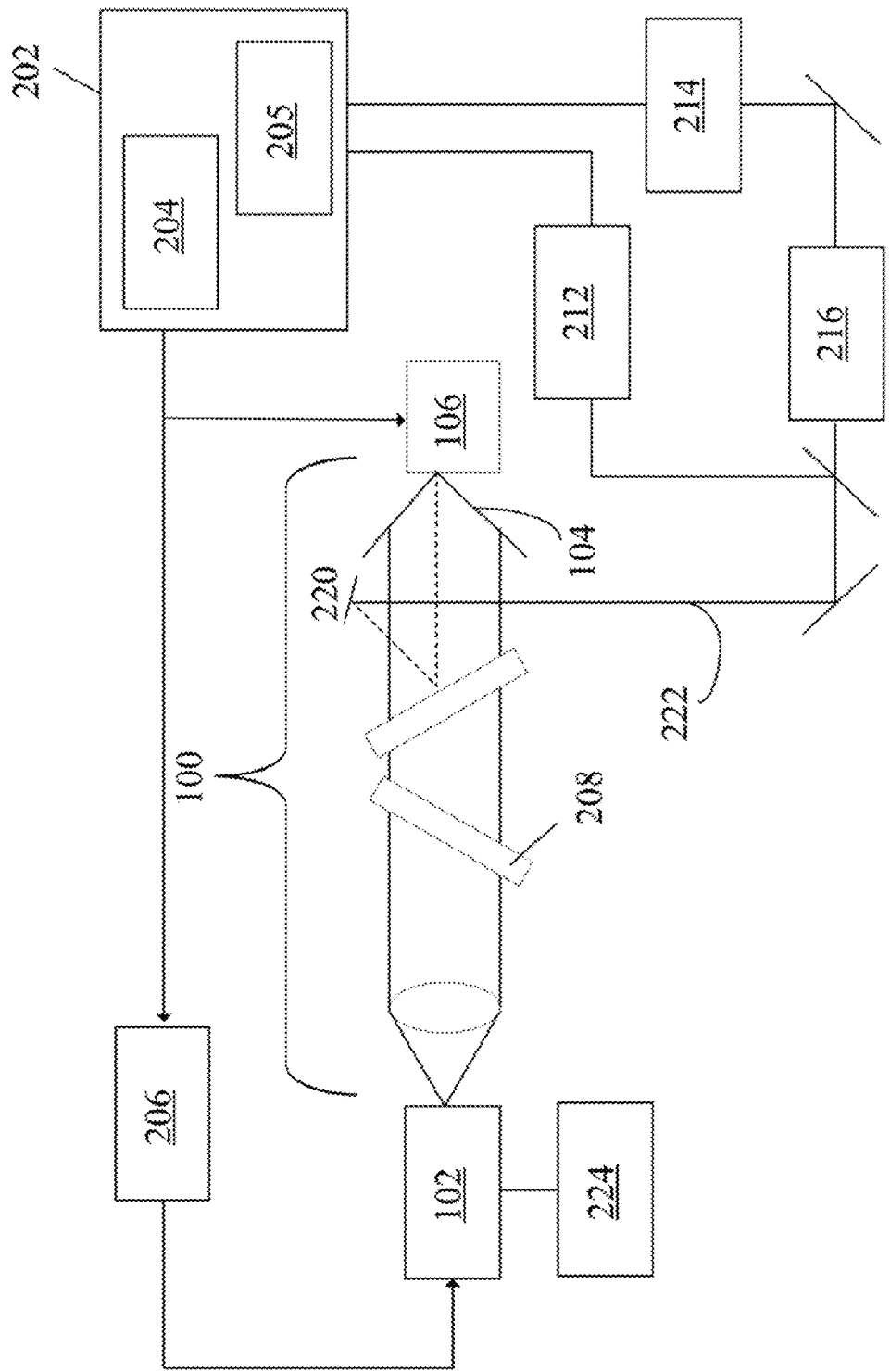
FIG. 1 illustrates an exemplary QCL-based gas analyzer system.

In one aspect, at least one retro-reflector (also known as a corner cube) replaces the traditional flat mirror structure for aligning a QCL beam in a gas analyzer system. FIG. 1 illustrates an exemplary QCL-based gas analyzer system. As shown, an external cavity 100 is defined by a QCL source 102 and at least one retro-reflector 104 generally aligned with the QCL source 102. In alternative embodiments, laser sources other than a QCL source can be used to generate radiation (e.g., infrared radiation) in the external cavity 100. The retro-reflector 104 can be supported on a motion mechanism 106, such as a flexing parallelogram, a motor, or piezoelectric crystals. Linear motion of the retro-reflector 104 can be achieved by applying a current or voltage to the motion mechanism 106, such as applying a current to the coil of a linear motor or voltage to piezoelectric crystals, for example. The retro-reflector 104 can be positioned in the external cavity 100 such that its apex is close to the center of the incident beam generated by the QCL source 102. In operation, the retro-reflector 104 is configured to receive an incident beam of radiation from the QCL source 102 and reflect the beam back to the QCL source 102 in about the same direction as the incident beam, thereby causing the radiation in the external cavity 100 to achieve a certain wavelength that is dependent on one or more of the following factors: i) properties of the QCL source 102, ii) components in the external cavity 100 (e.g., insertion of one or more etalons 208) and/or iii) the length of the external cavity 100 defined by the position of the retro-reflector 104 in relation to the QCL source 102. The retro-reflector 104 can maintain beam alignment even if it tilts or shears slightly during motion.

The radiation generated in the external cavity 100 based on the QCL source 102 and the retro-reflector 104 can be used to detect, identify and/or quantify specific gases in a gas sample. Generally, the radiation can be introduced to a particular sample and, as the radiation passes through the sample, specific wavelengths of the radiation are absorbed by molecules within the sample. The specific wavelengths of radiation that are absorbed are unique to each of the molecules within the sample. By identifying which wavelengths of radiation are absorbed and how much of the energy carried by these wavelengths is absorbed, it is therefore possible to determine, for example, the molecular composition of the sample and the concentration of specific molecules within the sample, respectively.

As shown in FIG. 1, an automated control system, including a data acquisition module 202, a power supply 206, a reference detector 212, and a signal detector 214, can be used to direct at least a portion of the radiation produced in the external cavity 100 through a gas cell 216 for determining the property of the gas sample contained in the gas cell 216. In some embodiments, the control system can adjust properties associated with the QCL source 102 and/or the retro-reflector 104 to achieve a desired wavelength or wavelength range of the radiation in the external cavity 100, such that the radiation can be easily absorbed by molecules in a gas sample in the cell 216. As shown, the data acquisition module 202 can comprise a waveform generator 204 and an analog-to-digital converter 205. The waveform generator 204 can transmit a signal to a power supply 206 (e.g., including a current and/or voltage driver) to instruct the power supply 206 to sweep the current and/or voltage supplied to the QCL source 102 over a controlled range. The waveform generator 204 can also transmit a signal to the retro-reflector 104, where the signal interacts with the motion mechanism 106 of the retro-reflector 104 to move the retro-reflector 104 back and forth in relation to the QCL source 102 (i.e., in a direction collinear to the incident beam generated by the QCL source 102, such as closer or further away from the QCL source 102). The synchronous tuning of the QCL source 102 and the retro-reflector 104, as controlled by the data acquisition module 202, can cause the lasing wavelength of the QCL source 102 to vary over a controlled wavelength range without mode hopping.

In some embodiments, one or more silicon-based etalons 208 are inserted in the beam path between the QCL source 102 and the retro-reflector 104 to confine the range of wavelengths that can be lased. In some embodiments, a thermoelectric cooler 224, in thermal communication with the QCL source 102, is used to stabilize the QCL source 102. In some embodiments, a moderately high-frequency, short-distance dither can be imposed on the retro-reflector 104 in addition to the sweep described above to create wavelength modulation of the QCL source 102. This brings the reflected beam to a higher frequency range away from the low-frequency noise associated with i) air turbulence on the QCL source 102, ii) 1/f noise of detectors and electronics, and/or iii) 60 Hz (and multiples) noise from other electronics.

A beam splitter 220 can be used to tap off/extract some of the radiation in the cavity 100 and direct the tapped (extracted) beam 222 for transmission to i) a reference detector 212 and/or ii) a signal detector 214 via the gas cell 216. A reference signal generated by the reference detector 212 based on the tapped beam 222 can be used by the data acquisition module 202 to compensate for energy change of the radiation in the external cavity 100. A sample signal generated by the signal detector 214 can be used by the data acquisition module 202 to detect changes due to absorption of energy by one or more gases in the gas cell 216 and determine the concentrations of the one or more gases in the gas sample. In some embodiments, signals generated by the reference detector 212 and/or the signal detector 214 are processed by the A/D converter 205 of the data acquisition module 202.

The reference signal can be generated by the reference detector 212 based on the tapped beam 222 as it travels through a reference gas, such as air. The data acquisition module 202 can use the reference signal to modulate one or more components of the external cavity 100 to achieve a desire wavelength of the radiation generated in the external cavity 100. For example, if the wavenumber of the tapped beam 222 as measured by the reference detector 212 differs from a desired wavenumber, the waveform generator 204 can interact with at least one of the power supply 206 or the retro-reflector 104 to adjust the wavelength of the radiation in the external cavity 100 such that the desired wavenumber is achieved. The amount of adjustment (i.e., the distance to move the retro-reflector 104 and/or the change in current or voltage produced by the power supply 206) is therefore a function of the difference in the actual and desired wavenumbers. In some embodiments, the data acquisition module 202 uses the following equation to determine the tuning distance of the retro-reflector 104 for generating radiation of a specific wavelength:

($\Delta v/v$)*external_cavity_length, where $v$ represents a wavenumber of the tapped beam 222, $\Delta v$ represents the amount of wavenumber change desired, and external_cavity_length represents the current length of the external cavity extending from the QCL source 102 to the retro-reflector 104. The tuning distance represents the lateral distance for moving the retro-reflector 104 from its current position to a desired position in relation to the QCL source 102. As an example, the amount of motion required to tune the wavelength over about 0.5 cm$^{-1}$ from 1280 cm$^{-1}$ in a cavity of about 30 cm long is about 0.12 mm ((0.5 cm$^{-1}$/1280 cm$^{-1}$)*30 cm=0.12 mm). In view of such a minimal distance, the support mechanism for the retro-reflector 104 can be flexure-based and thus have long lifetime.

Figure 2:
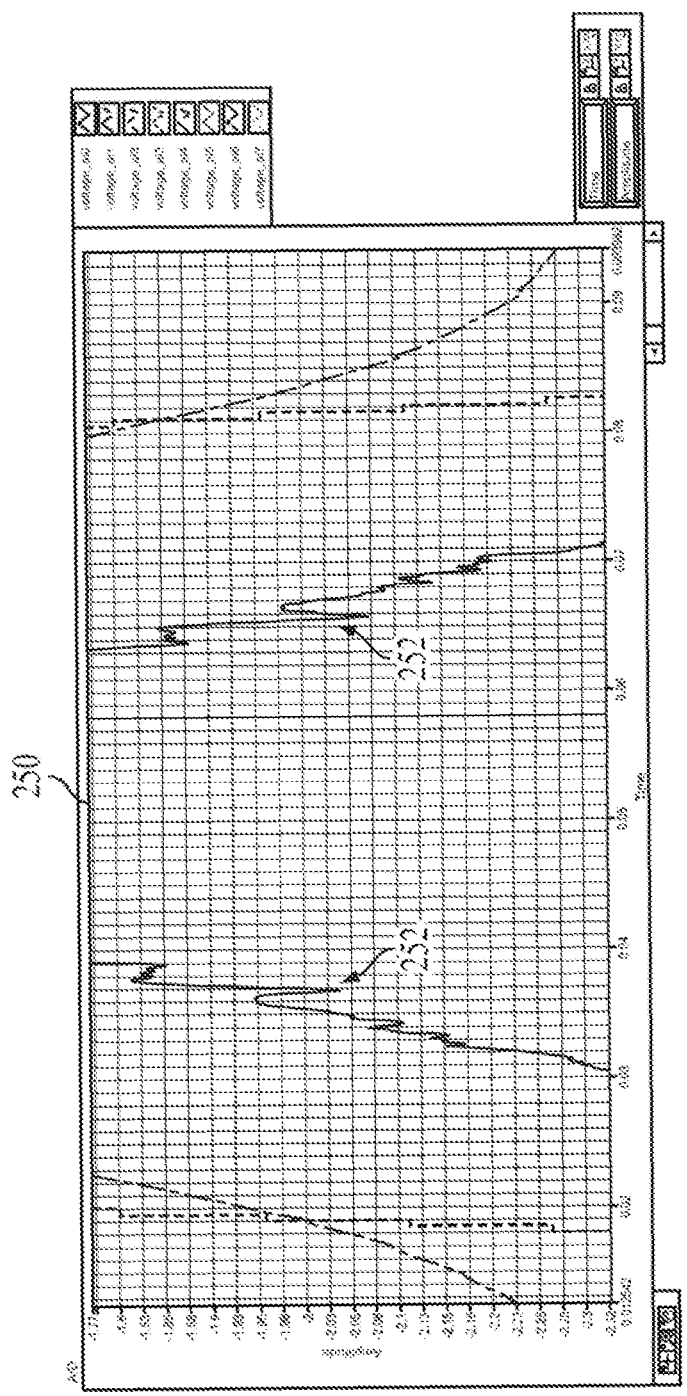
FIG. 2 illustrates an exemplary gas absorption diagram recorded by the control system of FIG. 1.

The sample signal is generated by the signal detector 214 based on the tapped beam 222 after it propagates through sample cell 206. The data acquisition module 202 can use the sample signal to determine the concentration of one or more gases in a gas sample stored in the gas cell 216. The sample signal produced by the detector 214 can be a variable, time-dependent signal. This sample signal can be represented as a gas absorption diagram that plots the magnitude/intensity of the energy absorbed by or transmitted through the sample in the cell 206, from which the concentration of one or gases in the sample can be determined. FIG. 2 illustrates an exemplary gas absorption diagram 250 recorded by the control system of FIG. 1 based on the sample signal generated by the signal detector 214. The absorption diagram 250 is generated from 50 ppm of $CH_4$ at 26 torr in a 5 m gas cell. At this pressure, the gas line is on the order of about 0.007 cm$^{-1}$ full width half max (FWHM). Had the QCL source 102 been mode hopping with a spacing ~0.015 cm$^{-1}$, the peaks 252 would have been missed. Instead, the QCL-based gas analyzer system of FIG. 1 is able to capture these peaks 252 by providing a robust, mode hop free light source for analyzing the gas sample.

With continued reference to FIG. 1, in some examples, at least one of the detectors 212 and 214 is an infrared detector. In some embodiments, the detectors 212 and 214 are cooled detectors. The data acquisition module 202 can receive signals from the detectors 212 and 214 and perform one or more of the following operations: (i) identify and provide a relative or absolute concentration of a particular material within a sample and/or (ii) adjust the external cavity 100 to achieve a desired radiation wavelength. The data acquisition module 202 can be, for example, signal processing hardware and/or quantitative analysis software that runs on a personal computer. The data acquisition module 202 can include a processing unit and/or memory. The data acquisition module 202 can continuously acquire and process data while computing the concentration of one or more gases within a sample. The data acquisition module 202 can transmit information, such as the identity of a sample component, the concentration of the sample component, and the wavenumber of the radiation extracted from the external cavity 100, to a display (not shown). The data acquisition module 202 can save information in graphical and tabular formats (e.g., in a format similar to the gas absorption diagram 250), and such data can be displayed as well.

Figure 3A:
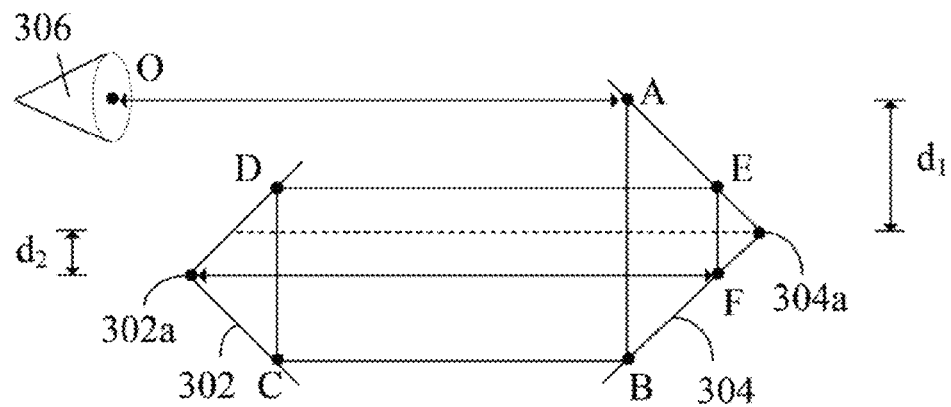
FIGS. 3A and B illustrate exemplary external cavities with at least two retro-reflectors.

In some embodiments, multiple retro-reflectors are used in the external cavity 100 of FIG. 1 to reduce the tuning distance required to obtain a certain radiation wavelength. The retro-reflectors can be arranged to increase the optical path length gain (i.e., the effective path length gain of the beam), thereby reducing the tuning distance of the retro-reflectors in relation to the QCL source 102, which reduces the amount of power required to move the retro-reflectors. FIGS. 3A and B illustrate exemplary external cavities with at least two retro-reflectors. Each exemplary external cavity can be implemented in the analyzer configuration of FIG. 1 to generate radiation of desired wavelength(s).

In FIG. 3A, two retro-reflectors 302, 304 are positioned such that their apexes 302a, 304b are both coplanar with the incident beam generated by a QCL source 306. The folded beam path is as follows: from point O at the QCL source 306, to point A of retro-reflector 304, to point B of retro-reflector 304, to point C of retro-reflector 302, to point D of retro-reflector 302, to point E of retro-reflector 304, to point F of retro-reflector 304 and finally to apex 302a of retro-reflector 302 (due to the two-dimensional nature of FIG. 3A, intermediate reflections within each retro-reflector 302, 304 are not shown). Thereafter, the beam retraces itself through the same path. Distance $d_1$ represents the normal distance between apex 304a of retro-reflector 304 and the line of incident beam (i.e., the line from point O to point A). Distance $d_2$ represents the offset distance in the direction normal to the incident beam between apex 302a of retro-reflector 302 and apex 304a of retro-reflector 304. The relationship between $d_1$ and $d2$ is such that $d2=d_1n$, where n is a positive integer and represents the number of different reflective paths the incident beam travels between the two retro-reflectors 302 and 304 before retracing itself. For example, the configuration of FIG. 3A shows 3 different reflective paths (i.e., n=3).

Figure 3B:
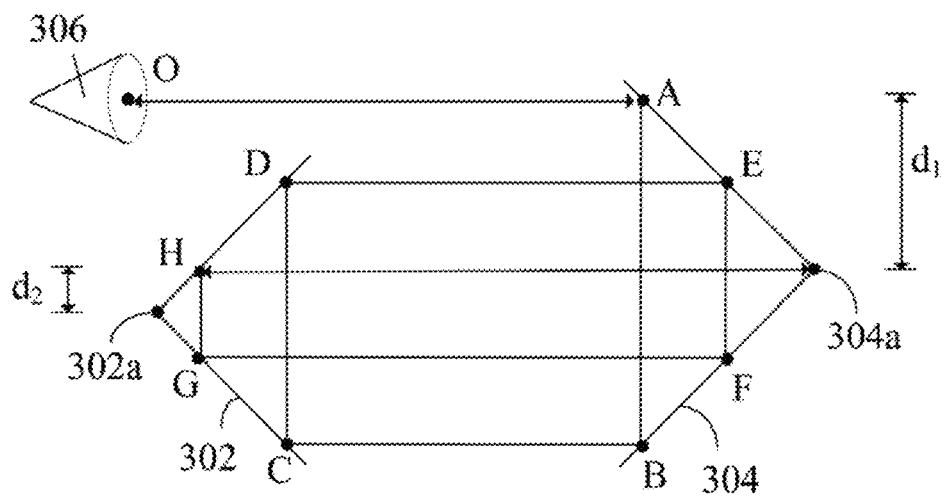

FIG. 3B shows a rearrangement of the two retro-reflectors 302, 304 by adjusting distances $d_1$ and $d_2$ to introduce 4 different reflective paths of the incident beam between the two retro-reflectors. Specifically, the folded beam path is as follows: from point O at the QCL source 306, to point A of retro-reflector 304, to point B of retro-reflector 304, to point C of retro-reflector 302, to point D of retro-reflector 302, to point E of retro-reflector 304, to point F of retro-reflector 304, to point G of retro-reflector 302, to point H of retro-reflector 302 and finally to apex 304a of retro-reflector 304. Thereafter, the beam retraces itself through the same path. In this configuration, the number of different reflective paths (n) between the two retro-reflectors 302 and 304 is 4. Therefore, FIGS. 3A and B show that distances $d_1$ and $d_2$ can be appropriately adjusted to achieve a desired number of reflective paths (n) between a pair of retro-reflectors.

Such folded beam geometry is advantageous in a laser system where laser path length requires periodic adjustment. As an example, assume that a system with a single retro-reflector requires moving the retro-reflector to a certain distance collinear with respect to the QCL beam in order to obtain a desired beam wavelength. This distance can be reduced by a factor proportional to the optical path length gain achieved by using multiple retro-reflectors. The optical path length gain is in turn proportional to n, the number different reflective paths between the retro-reflectors. For a two retro-reflector configuration, such as the configurations shown in FIGS. 3A and B, Table 1 lists the correlation between n and the optical path length gain for each of retro-reflectors 302, 304.

TABLE 1

| N | Optical path length gain for retro-reflector 304 | Optical path length gain for retro-reflector 302 |
| --- | --- | --- |
| 1 | 4 | 2 |
| 2 | 6 | 4 |
| 3 | 8 | 6 |
| 4 | 10 | 8 |
| N | 2n + 2 | 2n |

Therefore, at a higher modulation rate, less motion of the retro-reflectors are required if multiple retro-reflectors are used. This means lower acceleration and forces can be applied to the retro-reflectors. In embodiments involving multiple retro-reflectors, one of the retro-reflectors can be used for wavelength tuning while another can be used for high-frequency modulation. In embodiments involving multiple retro-reflectors, because the beam in the external cavity strikes the apex of one of the retro-reflectors (e.g., apex 302a in FIG. 3A or apex 304a in FIG. 3B), the beam can be inverted during the retracing, thereby significantly reducing, even eliminating, any first-order aberrations introduced in the retro-reflectors. In general, the multi-retro-reflector configuration can be optimal when applied to highly-collimated, small-area beams, such as lasers.

Figure 4:
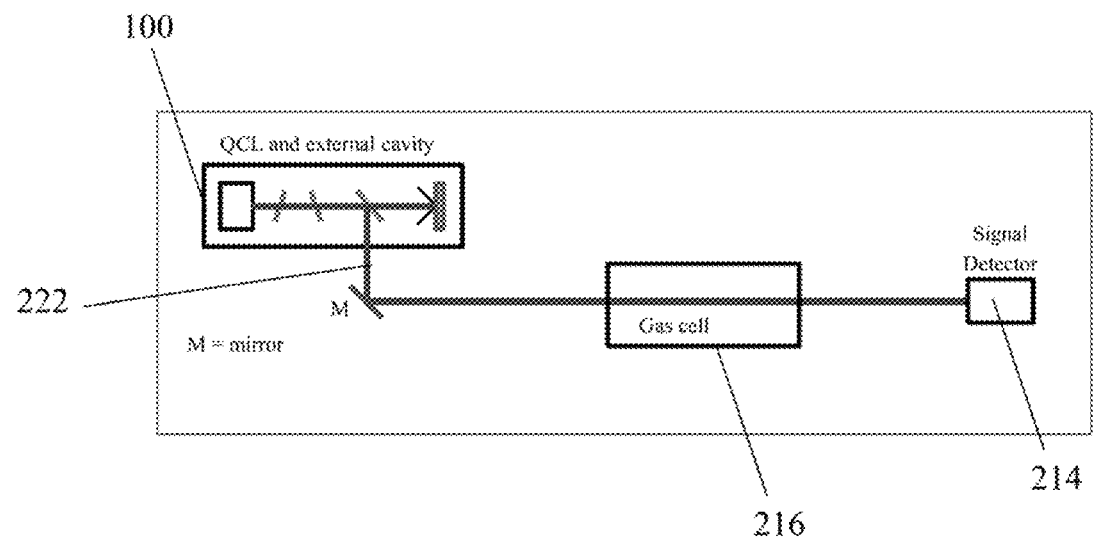
FIG. 4 illustrates a simplified gas analyzer system of FIG. 1 configured for absorbance measurement.

FIG. 4 illustrates a simplified gas analyzer system of FIG. 1 configured for absorbance measurement of a sample. As shown, a beam of radiation 222 is tapped from the external cavity 100 and transmitted through the gas cell 216. The tapped beam 222, after propagating through the gas cell 216, is received by the signal detector 214, which generates a sample signal. While not illustrated, the gas analyzer system can include the data acquisition module 202 to calculate the concentration of one or more substances in the gas sample stored in the gas cell 216 based on the intensity (e.g., amplitude) of absorption measured by the sample signal. The system can also include the reference detector 212 for detecting and measuring properties of the tapped beam 222 from the external cavity 100 as it propagates through a reference gas. A reference signal can be generated by the reference detector 212 to calibrate the external cavity 100 for ensuring that the desired wavelength or wavelength range is maintained.

Figure 5:
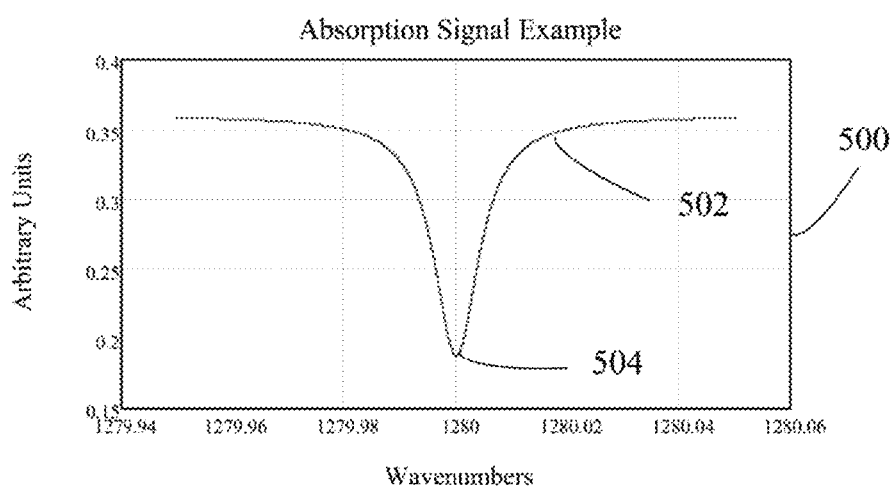
FIG. 5 illustrates an exemplary gas absorption diagram generated from the gas analyzer system of FIG. 4.

FIG. 5 illustrates an exemplary gas absorption diagram generated from the gas analyzer system of FIG. 4. The gas absorption diagram 500 is a plot of the sample signal 502 generated by the signal detector 408 over a controlled range of wavelengths. Specifically, the absorption diagram 500 represents the absorption energy of a gas molecule (i.e., an absorber) in the sample cell 216 as the beam 222 is scanned over a range of wavenumbers. The absorber of this example has an absorption maximum at a wavenumber of about 1280 centered at the dip 504 and the absorber is mixed in dry air with a total pressure of 25 torr or about 1/30 of an atmosphere. Because molecules absorb energy at specific wavenumber regions and the width of each wavenumber region over which they absorb depends partially on the total pressure of the gas they are mixed in, an absorption diagram (e.g., the absorption diagram 500) can be used to identify the molecules in the sample mixture.

In some embodiments, instead of measuring the concentration of one or more gases in a gas sample based on the intensity/magnitude of radiation absorption at certain wavelengths, control systems of the present technology can also determine gas concentrations in a sample based on phase changes of the radiation beam (i.e., changes in the real part of the index of refraction or in the speed of light) as the beam propagates through the sample at certain absorption wavelengths, such as in the vicinity of the absorption wavelengths. In general, phase measurements are less noisy than amplitude measurements. Therefore, the concentrations of one or more gases in a gas sample can be measured more accurately using phase measurements than using amplitude measurements.

Figure 6:
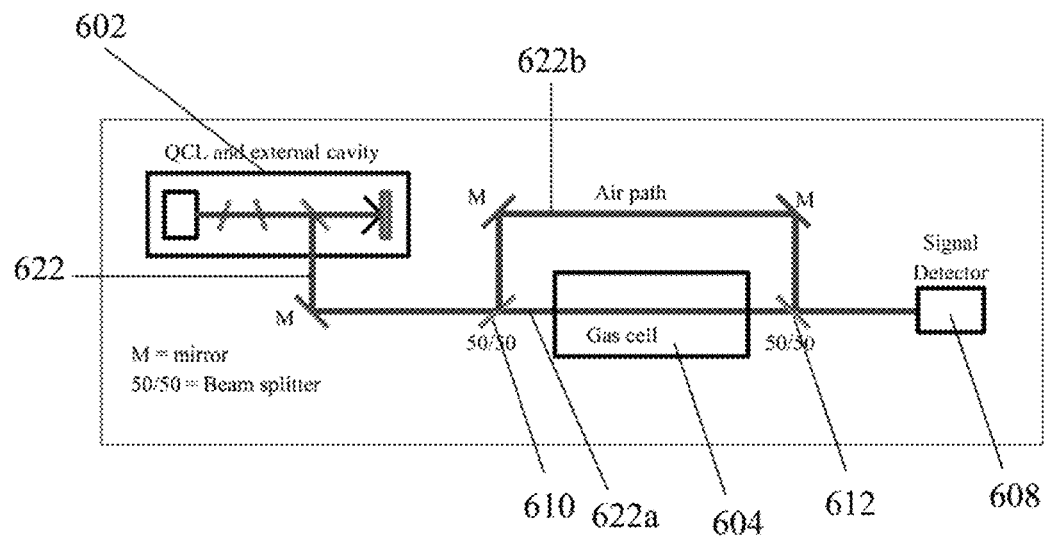
FIG. 6 illustrates an exemplary gas analyzer system configured for determining the concentrations of one or more gases in a sample using phase measurements.

FIG. 6 illustrates an exemplary gas analyzer system configured to determine the concentrations of one or more gases (i.e., absorbers) in a sample using phase measurements. In a first experiment, a beam of radiation 622 is tapped from an external cavity 602 (similar to the external cavity 100 of FIG. 1) and tapped again at beam splitter 610 to generated a reference beam of radiation 622b and a sample beam of radiation 622a. The sample beam of radiation 622a is transmitted through a gas cell 604 containing a sample of one or more absorbers. In addition, the reference beam 622b can be transmitted through a reference cell (not shown) containing a reference gas, such as air. The sample beam of radiation 622a at the output of the gas cell 604 and the reference beam of radiation 622b at the output of the reference cell can be recombined at a beam splitter 612 to allow the two beams to interfere with each other to create a first recombined beam of radiation, which is received by a signal detector 608, based on which a first recombined signal is generated. In general, by interfering the two beams 622a and 622b, the system allows the light to constructively or destructively interfere depending on the distance (or time) difference between the two paths and the speed of the light. In some embodiments, the reference cell is absent from the system of FIG. 6, in which case the reference beam travels along a reference path through air to arrive at the beam splitter 612.

In a separate experiment using the same system configuration of FIG. 6, the reference beam 622b can be transmitted through the same path of the same path length as the first experiment (e.g., through a reference cell containing the same reference gas), while the sample beam 622a is transmitted through the gas cell 604 that now contains no absorber (e.g., containing only air). The sample beam 622a at the output of the gas cell 604 and the reference beam 622b can be recombined at the beam splitter 612 to generate a second recombined beam, which is received by the signal detector 608, based on which a second recombined signal is generated. Using the first and the second recombined signals, the concentration of one or more absorbers in the cell 604 (i.e., from the first experiment) can be calculated by determining the phase difference between the signals near certain absorption wavelengths. Such analysis can be performed by a processor (not shown), similar to the data acquisition module 202 of FIG. 1.

Figure 7:
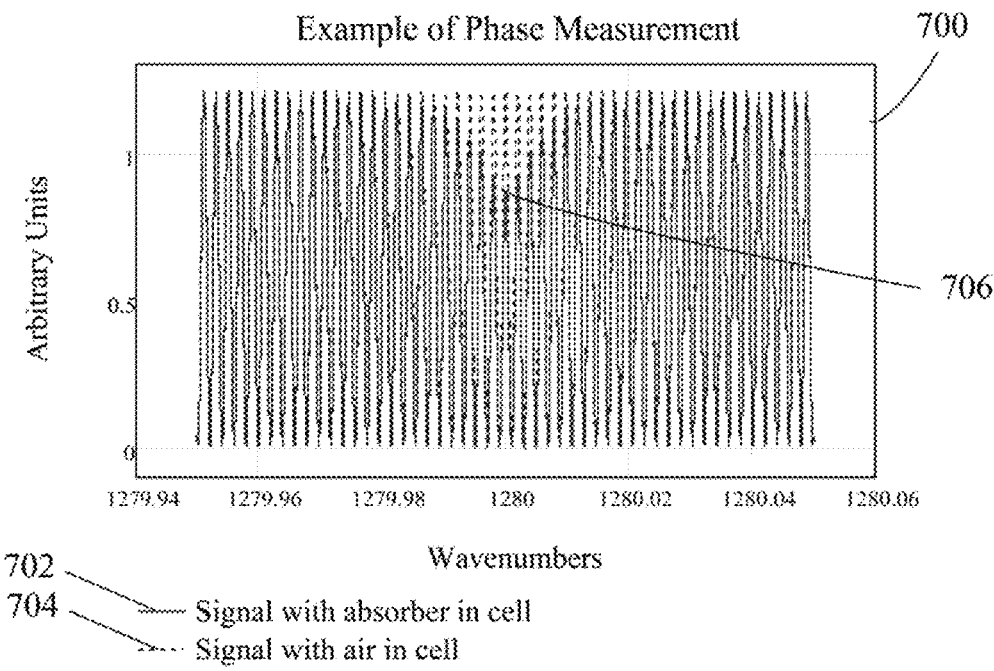
FIG. 7 illustrates an exemplary phase measurement diagram generated from the gas analyzer system of FIG. 6.

FIG. 7 illustrates an exemplary phase measurement diagram generated from the gas analyzer system of FIG. 6 from which phase difference is extracted. Specifically, the phase measurement diagram 700 shows the plot of the first recombined signal 702 that represents interference measurement of the first recombined beam corresponding to having at least one absorber in the gas cell 604 (i.e., from the first experiment). In addition, the phase measurement diagram 700 shows the plot of the second recombined signal 704 that represents interference measurement of the second recombined beam corresponding to having no absorber in the gas cell 604 (i.e., from the second experiment). Both the signals 702 and 704 are plotted over a controlled range of wavelengths expressed in the unit of wavenumber. In addition to the amplitude change of the first recombined signal 702 around wavenumber 1280 (at the dip 706) due to energy absorption by the absorber in the cell 604 from the sample beam 622a, the sinusoids of the first recombined signal 702 are offset laterally compared to the recombined signal 704 due to changes in the index of refraction of the sample beam 622a. Such phase difference in the signals 702 and 704 forms the basis for determining the concentration of the one or more absorbers in the gas sample.

Figure 8:
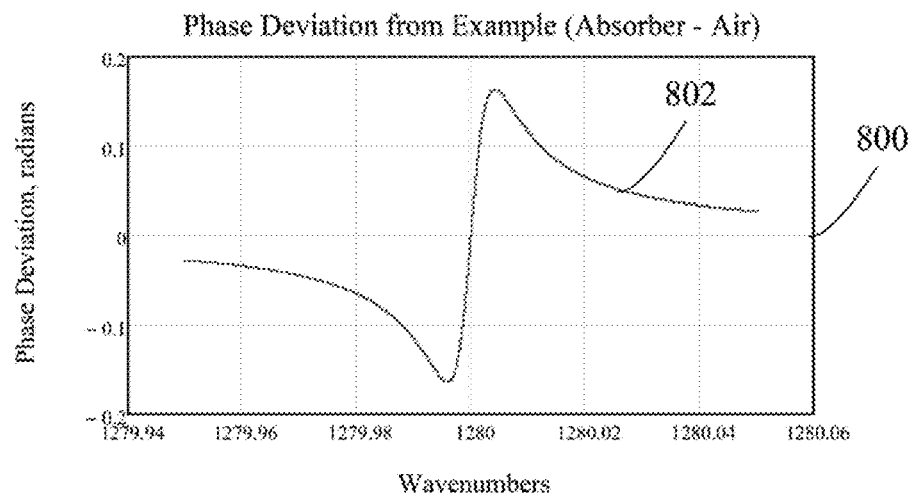
FIG. 8 illustrates a phase deviation diagram determined based on the phase measurement diagram of FIG. 7.

FIG. 8 illustrates a phase deviation diagram determined based on the phase measurement diagram of FIG. 7. The phase deviation waveform 802 of the diagram 800 represents the difference in phase between the first recombined signal 702 and the second recombined signal 704 (corresponding to experiments with and without an absorber in the sample cell 604, respectively) over a range of wavelengths. The phase deviation waveform 802 can be used to determine the concentration of at least one absorber in the gas cell 604, where the amount of phase deviation is directly proportional to the gas concentration. In general, the second recombined signal 704 allows the system to discount phase effects introduced by system components other than the phase (index of refraction) of the gas in the sample cell 604, thereby providing a more accurate determination of the concentration of the absorber in the gas sample.

In some embodiments, information captured by the second recombined signal 704 can be used to calibrate the external cavity 602 for ensuring that the desired wavelength or wavelength range is maintained by the beam 622, similar to the calibration process described above with reference to FIG. 1.

Figure 9:
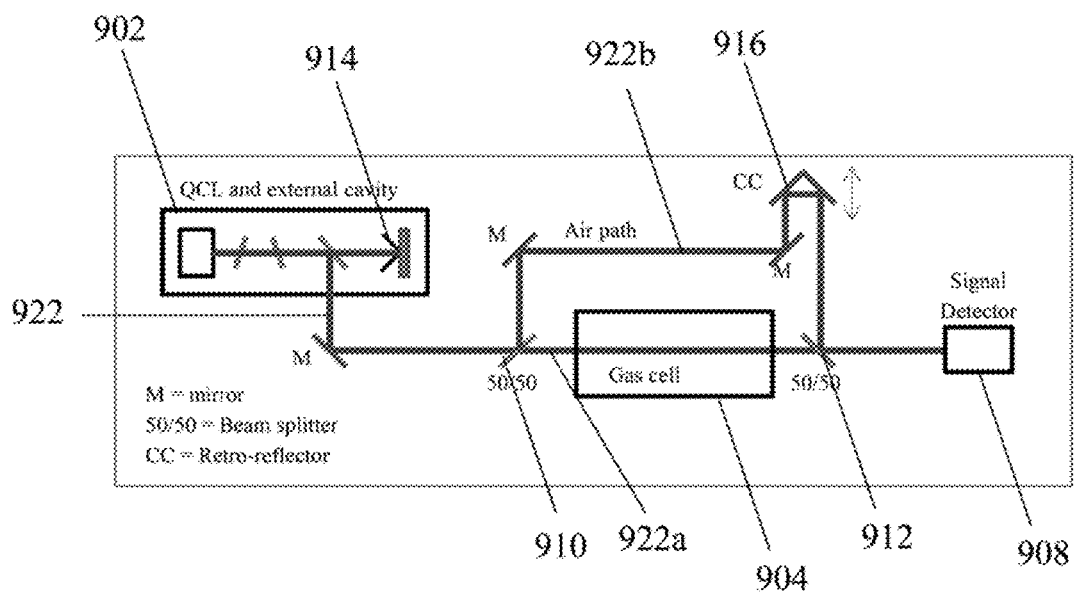
FIG. 9 illustrates an exemplary gas analyzer system configured for phase measurement with phase modulation using a retro-reflector.

FIG. 9 illustrates an exemplary gas analyzer system configured for phase measurement with phase modulation using a retro-reflector. In a first experiment, a beam of radiation 922 is tapped from an external cavity 902 (similar to the external cavity 100 of FIG. 1) and split again at beam splitter 910 to generate a reference beam 922b and a sample beam 922a. The sample beam 922a is transmitted through a gas cell 904 containing a gas sample of one or more absorbers. In addition, the reference beam 922b can be transmitted through a reference cell (not shown) containing a reference gas, such as air. The sample beam of radiation 922a at the output of the gas cell 904 and the reference beam of radiation 922b at the output of the reference cell can be recombined at a beam splitter 912 to allow the two beams to interfere with each other to create a first recombined beam, which is received by a signal detector 908, based on which a first recombined signal is generated. In some embodiments, the reference cell is absent from the system of FIG. 9, in which case the reference beam travels along a reference path through air to arrive at the beam splitter 912.

A retro-reflector 916 positioned along the path of the reference beam 922b outside of the external cavity 902 can be used to modulate the path length of the reference beam 922b as it travels through the reference cell containing the reference gas (or an air path without the reference cell). Specifically, the retro-reflector 916 can be used to modulate the repetitive pattern (e.g., a sinusoidal pattern) of the reference beam 922b to a higher frequency. This offers several advantages, including allowing the resulting phase measurement to be analyzed more frequently and bringing the frequency range away from the low-frequency noise (e.g., 1/f noise of detectors and other electronics). The retro-reflector 916 that is used to modulate the path length of the reference beam 922a is distinct from the retro-reflector 914 used in the external cavity 902 to modulate the wavelength of the QCL radiation. To modulate the path length of the reference beam 922a, the motion of the retro-reflector 916 can be adjusted to achieve certain desired frequency or frequency range. For example, the retro-reflector 916 can be oscillated in a direction collinear to the beam entering and/or exiting the retro-reflector 916 to change the path length of the reference beam 922b. Because the phase of the recombined signals measured at the detector 908 is a function of (1) wavelength and (2) the path difference between the sample beam 922a and reference beam 922b, changing the reference path length thus changes the recombined signals at the detector 908 to allow an increased number of phase determinations per time unit.

In a second experiment using the same system configuration of FIG. 9, the reference beam 922b can be transmitted through the same path as the first experiment (e.g., through a reference cell containing the same reference gas or through an air path without the reference cell), while the sample beam 922a is transmitted through the gas cell 604 that now contains no absorber (e.g., containing only air). The sample beam 922a at the output of the gas cell 904 and the reference beam 922b can be recombined at the beam splitter 912 to generate a second recombined beam, which is received by the signal detector 908, based on which a second recombined signal is generated. In some embodiments, the modulation of the retro-reflector 916, including the path length of the reference beam 922b, is consistent for both the first and second experiments. That is, the path length of the second beam 922b is the same for both experiments.

Based on the first and second recombined signals, a processor (not shown) can calculate the concentration of one or more absorbers in the sample cell 904 (i.e., from the first experiment) by determining the phase change of the two signals near certain absorption wavelengths, similar to the approach described above with respect to the phase measurement diagram 700 of FIG. 7 and the phase deviation diagram 800 of FIG. 8. In some embodiments, information captured by the second recombined signal can be used to calibrate the external cavity 902 for ensuring that the desired wavelength or wavelength range is maintained by the beam 922, similar to the calibration process described above with reference to FIG. 1. The gas analyzer system of FIG. 9 shows that retro-reflectors can be used not only in an external cavity to modulate the wavelength of a beam of radiation used to scan a gas sample, but also in a beam path outside of the external cavity to modulate the phase of the recombined signals.

Figure 10:
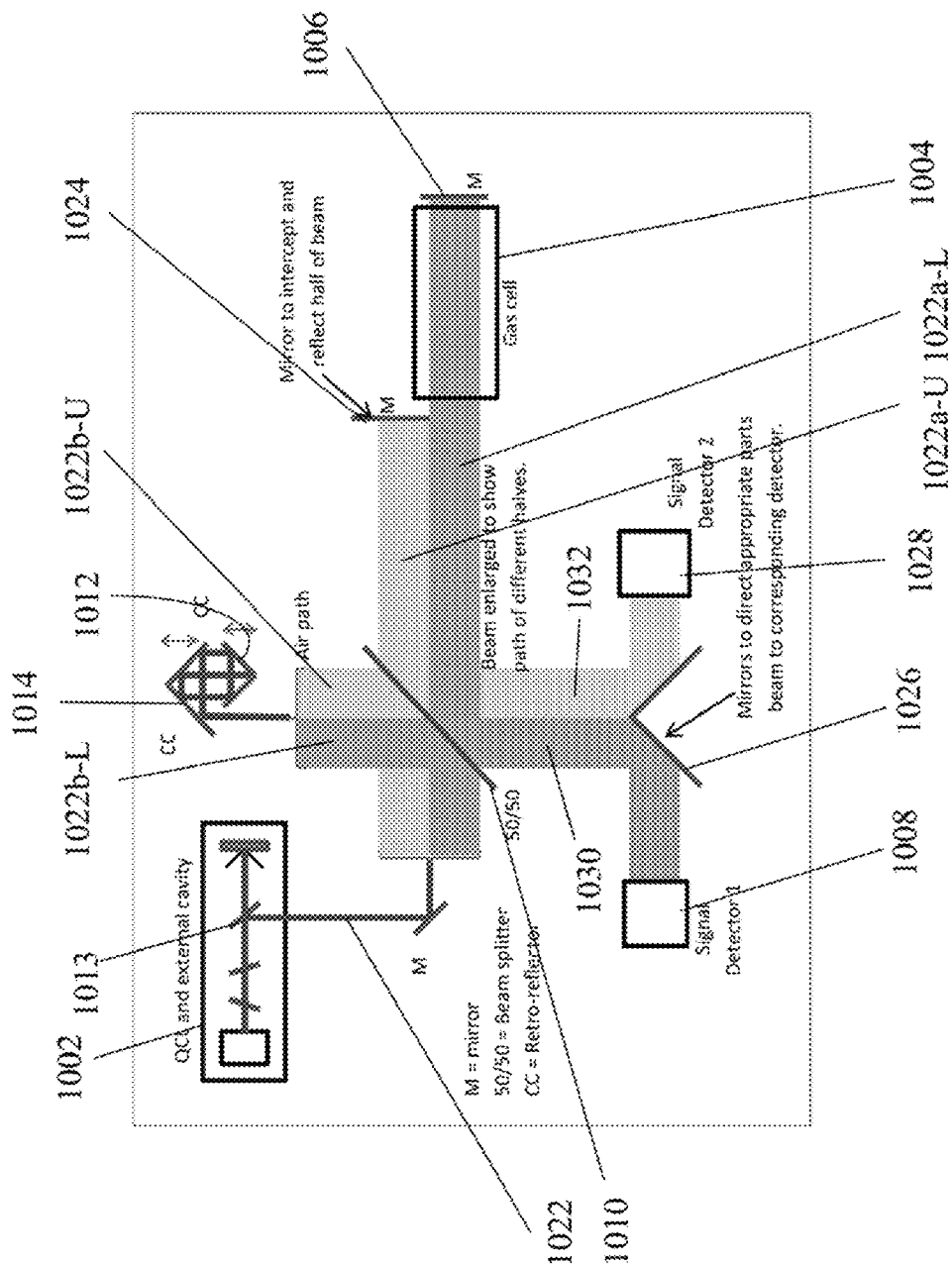
FIG. 10 illustrates an exemplary gas analyzer system configured for phase measurement and phase modulation using multiple retro-reflectors.

FIG. 10 illustrates an exemplary gas analyzer system configured for phase measurement with phase modulation using multiple retro-reflectors. The system of FIG. 10 functions similarly to the system of FIG. 9. One difference is that instead of running two separate experiments on the configuration of FIG. 9 to determine the first and second recombined signals, the configuration of FIG. 10 allows one experiment to be performed to generate both of the signals, thereby saving time and cost. Another difference is that more than one retro-reflector is used in the system of FIG. 10 to modulate the path length of the reference beam.

In operation, radiation is generated in the external cavity 1002 (similar to the external cavity 100 of FIG. 1) and a portion of the beam 1022 is tapped off at beam splitter 1013 and transmitted to another beam splitter 1010. As the beam 1022 approaches a section of the beam splitter 1010 (i.e., the lower half of the beam splitter 1010), a portion of the beam 1022 (herein referred to as reference beam 1022b-L) travels toward the two retro-reflectors 1012 and 1014 and another portion of the beam 1022 (herein referred to as sample beam 1022a-L) travels toward the gas cell 1004. Specifically, the sample beam 1022a-L traverses through the gas cell 1004, is reflected by the mirror 1006 positioned at the output of the gas cell 1004, and recombines with the reference beam 1022b-L after it is reflected by the retro-reflectors 1012 and 1014. The recombination of the beams 1022a-L and 1022 b-L can occur at the same section of the beam splitter 1010 where the two beams are initially generated (i.e., the lower half of the beam splitter 1010). The resulting first recombined beam 1030 is then intercepted by a mirror 1026 (e.g., at the left half of the mirror 1026), which forwards the first recombined beam 1030 to a signal detector 1008, based on which the first recombined signal is generated. In addition, as the beam 1022 approaches another section of the beam splitter 1010 (i.e., the upper half of the beam splitter 1010), a portion of the beam 1022 (herein referred to as reference beam 1022b-U) travels toward the two retro-reflectors 1012 and 1014 and another portion of the beam 1022 (herein referred to as sample beam 1022a-U) travels toward the mirror 1024 that is positioned at the input of the gas cell 1004. The sample beam 1022a-U does not traverse through the sample cell 1004 and instead, is reflected by the mirror 1024 to recombine with the reference beam 1022b-U after it is reflected by the retro-reflectors 1012 and 1014. The recombination of the beams 1022a-U and 1022 b-U can occur at the same section of the beam splitter 1010 where the two beams are initially generated (i.e., the upper half of the beam splitter 1010). The resulting second recombined beam 1032 is then intercepted by the mirror 1026 (e.g., at the right half of the mirror 1026), which forwards the second recombined beam 1032 to a signal detector 1028, based on which the second recombined signal is generated.

The phase variation between the first and second recombined signals can then be used by a processor (not shown) to determine the concentration of one or more absorbers in the gas sample of cell 1004, similar to the approach described above with respect to the phase measurement diagram 700 of FIG. 7 and the phase deviation diagram 800 of FIG. 8. In some embodiments, the processor can be substantially similar to the processor 202 of FIG. 1. In some embodiments, information captured by the second recombined signal can be used to calibrate the external cavity 1002 to ensure that the desired wavelength or wavelength range is maintained by the beam 1022, similar to the calibration process described above with reference to FIG. 1.

As shown in FIG. 10, two retro-reflectors 1012 and 1014, positioned in a beam path outside of the external cavity 1002, are used to modulate the path length of the reference beam 1022b. The functions and advantages of using multiple retro-reflectors with respect to a beam of radiation is described above with reference to FIGS. 3A and B. For example, similar to the wavelength modulation for the laser, the multiple retro-reflectors do not have to move as far to create path length changes in the reference beam 1022b. In some embodiments, the positions of the retro-reflectors 1012 and 1014 in the beam path can be individually oscillated to achieve the desired frequency or frequency range. That is, one or both of the retro-reflectors 1012 and 1014 can be made to oscillate at the same or different frequencies so as to modulate the path length of the reference beam 1022b and thus modulate the phase of the recombined beams received by the detectors 1008 and 1028. In some embodiments, if both of the retro-reflectors 1012 and 1014 oscillate, they move in directions opposite to each other. In some embodiments, three or more retro-reflectors can be used to further enhance path length modulation of the reference beam 1022b.

As described above with reference to FIGS. 6, 9 and 10, the concentration of a gas (i.e. absorber) in a sample can be determined from the phase difference between a first and second recombined signals corresponding to measurements taken with and without an absorber in the sample cell, respectively. The following exemplary set of equations can be used to determine the first recombined signal Sig(t) as a function of time:

$$Sig(t) = A(t)\cos(2\pi \cdot OPD(t) \cdot v(t) + \phi_{arb}),$$

where $$OPD(t) = (2 \cdot n_{ext}(v(t)) \cdot Z_{ext} + n_g(v(t)) \cdot Z_g - (2 \cdot n_{ext}(v(t)) \cdot (Z_{cc} + \Delta Z_{cc}(t))).$$

In these equations, function $A(t)$ represents the amplitude variations over time from changes in optical power, beam splitter(s), absorptions in gas, mirror efficiencies, etc. In addition, $v(t)$ represents the wavenumber output of the radiation from the external cavity (e.g., the radiation 922 from the external cavity 902 of FIG. 9) as a function of time, and $\phi_{arb}$ represents the arbitrary phase from optical and electrical components. Furthermore, $n_{ext}(v(t))$ represents the real part of index of refraction in the external radiation path (e.g., the path of the reference beam 922b of FIG. 9) as a function of wavenumber, $Z_{ext}$ represents the external radiation path length (e.g., the path length of the reference beam 922b of FIG. 9), $n_g(v(t))$ represents the real part of index of refraction of a sample in the gas cell (e.g., the gas cell 904 of FIG. 9) as a function of wavenumber, $Z_g$ represents the path length of the radiation in the gas cell (e.g., the path length of the sample beam 922a in the gas cell 904), $Z_{cc}$ represents the average path of beam from a beam splitter (e.g., the beam splitter 910 of FIG. 9) to the last apex of the retro-reflector (e.g., the retro-reflector 916 of FIG. 9), and $\Delta Z_{cc}(t)$ represents the path length change from the motion of the retro-reflector (e.g., the retro-reflector 916) as a function of time. A similar equation can be used to represent the second recombined signal as a function of time. Using the equations for the first and second recombined signals, the phases of the signals and their differences can be determined, based on which the concentration of one or more absorbers in a gas sample can be calculated. Even though the equations are explained with reference to the system of FIG. 9, one of ordinary skill in the art understands that the equations can be easily adapted to apply to the systems of FIGS. 6 and 10 to determine the concentration of one or more absorbers in a sample cell.

It should also be understood that various aspects and embodiments of the invention can be combined in various ways. Based on the teachings of this specification, a person of ordinary skill in the art can readily determine how to combine these various embodiments. For example, in some embodiments, any of the aspects above can include one or more of the above features. One embodiment of the invention can provide all of the above features and advantages.

What is claimed is:

1. A system for monitoring at least one gas in a sample gas, the system comprising:
   a source for generating a beam of radiation;

at least one retro-reflector configured to receive the beam of radiation from the source in an incident direction and reflect the beam of radiation toward the source in alignment with the incident direction, thereby causing radiation in a cavity defined by the source and the at least one retro-reflector to obtain a desired wavelength;

a motor configured to move the at least one retro-reflector with respect to the source in a direction collinear with the incident direction;

a sample cell storing the sample gas comprising the at least one gas;

a beam splitter located external to the cavity, the beam splitter configured to split the at least a portion of the extracted beam of radiation into at least (i) a first beam of radiation directed through the sample cell and (ii) a second beam of radiation directed through a reference path;

a recombination device for interfering and recombining the first beam of radiation after traversing through the sample cell with the second beam of radiation to generate a first recombined beam of radiation;

a detector in optical communication with the sample cell, wherein the detector is configured to generate a first recombined signal at the output of the sample cell based on the first recombined beam of radiation; and a processor, in electrical communication with the detector, configured to determine a concentration of the at least one gas in the sample gas based on a phase difference between the first recombined signal and a second recombined signal.

2. The system of claim 1, wherein the processor is further configured to perform at least one of (i) transmit a first signal to a power supply to adjust a current or voltage provided to the source or (ii) transmit a second signal to the motor to move the retro-reflector by a distance, wherein at least one of the first or second signal modulates a wavelength of the radiation in the cavity to obtain the desired wavelength.

3. The system of claim 2, wherein the distance is determined as a function of (1) a wavenumber of the extracted beam of radiation, (2) an amount of wavenumber change desired in the extracted beam of radiation, and (3) a current distance between the source and the retro-reflector.

4. The system of claim 1, further comprising at least one silicon-based etalon located between the source and the retro-reflector in the cavity to confine the radiation in the cavity to within a desire wavelength range.

5. The system of claim 1, further comprising a plurality of retro-reflectors positioned to increase an optical path length gain of the radiation in the cavity, thereby minimizing a distance between the plurality of retro-reflectors and the source by an amount proportional to the optical path length gain.

6. The system of claim 5, wherein the plurality of retro-reflectors are configured to receive the beam of radiation from the source and generate a number of reflective beam paths in the cavity, the optical path length gain being proportional to the number of reflective beam paths.

7. The system of claim 6, wherein the plurality of retro-reflectors comprise a first retro-reflector and a second retro-reflector with a relationship defined by $d2=d1/n$, wherein (i) d1 represents a first normal distance between an apex of the first retro-reflector and the beam of radiation, (ii) d2 represents a second normal distance between an apex of the second retro-reflector and the apex of the first retro-reflector, and (iii) n represents the number of reflective beam paths.

8. The system of claim 7, further comprising adjusting at least one of the first normal distance (d1) or the second normal distance (d2) to change the number of reflective beam paths (n).

9. The system of claim 1, further comprising:
a reference gas on the reference path through which the second beam of radiation propagates,
wherein the recombination device comprises a second beam splitter for combining the first beam of radiation at the output of the sample cell and the second beam of radiation after traversing through the reference gas to generate the first recombined beam of radiation.

10. The system of claim 9, wherein the reference gas comprises air.

11. The system of claim 9, further comprising a second sample cell storing the reference gas, wherein the second sample cell is positioned along the reference path to allow the second beam of radiation to propagate therethrough.

12. The system of claim 9, wherein the detector is adapted to generate the second recombined signal based on a second recombined beam of radiation that is produced as a combination of (1) the first beam of radiation after traversing through the reference path and (2) the second beam of radiation after traversing through the sample cell without the sample gas stored therein.

13. The system of claim 1, further comprising one or more additional retro-reflectors located external to the cavity along the reference path to modulate a phase of the first recombined signal by changing a path length of the second beam of radiation.

14. The system of claim 1, further comprising:
a reference gas on the reference path through which the second and a fourth beams of radiation propagate, wherein the first, the second, a third, and the fourth beams of radiation are produced by the beam splitter based on the at least a portion of the extracted beam;
a first mirror positioned at an input of the sample cell that contains the sample gas, the first mirror adapted to receive the third beam of radiation and substantially reflect the third beam of radiation toward the beam splitter; and
a second mirror positioned at an output of the sample cell to receive the first beam of radiation and substantially reflect the first beam of radiation back through the sample cell toward the beam splitter;
wherein the recombination device comprises the beam splitter and the recombination device is adapted to (1) recombine the first and second beams of radiation to generate the first recombined beam and (2) recombine the fourth and third beams of radiation to generate a second recombined beam.

15. The system of claim 14, further comprising a third mirror adapted to receive (i) the first recombined beam of radiation and transmit the first recombined beam of radiation to the detector to generate the first recombined signal, and (ii) the second recombined beam of radiation and transmit the second recombined beam of radiation to a second detector to generate the second recombined signal.

16. A method for monitoring at least one gas in a sample gas, the method comprising:
generating a beam of radiation;
directing the beam of radiation to at least one retro-reflector along an incident direction within a cavity defined by the source and the at least one retro-reflector;
reflecting the beam of radiation by the at least one retro-reflector toward the source in a direction aligned with the incident direction, thereby causing radiation in the cavity to obtain a desired wavelength;

splitting the extracted beam of radiation into at least a first beam of radiation and a second beam of radiation;

directing the first beam of radiation from the cavity to propagate through a sample cell that stores the sample gas comprising the at least one gas;

directing the second beam of radiation through a reference path containing a reference gas;

interfering and combining the first beam of radiation and the second beam of radiation to generate a first recombined beam of radiation;

determining a concentration of the at least one gas in the sample gas based on a phase difference of the first recombined beam of radiation and a second recombined beam of radiation; and modulating a wavelength of the radiation in the cavity to obtain the desired wavelength, wherein modulating the wavelength comprises at least one of adjusting a current or voltage for generating the beam of radiation or moving the at least one retro-reflector by a distance collinear to the incident direction.

17. The method of claim 16, further comprising positioning a plurality of retro-reflectors in the cavity to receive the beam of radiation from the source and generate a number of reflective beam paths in the cavity.

18. The method of claim 17, wherein the reflective beam paths are collinear to the incident direction.

19. The method of claim 17, wherein an increase in the number of reflective beam paths in the cavity is adapted to increase an optical path length gain of the radiation in the cavity, thereby minimizing a distance between the plurality of retro-reflectors and the source.

20. The method of claim 16, further comprising:
generating a first recombined signal based on the first recombined beam of radiation.

21. The method of claim 20, further comprising:
replacing the sample gas in the sample cell with the reference gas;
directing the first beam of radiation through the sample cell; and
directing the second beam of radiation through the reference path;
combining the first beam of radiation and the second beam of radiation to generate the second recombined beam of radiation; and
generating a second recombined signal based on the second recombined beam of radiation.

22. The method of claim 21, further comprising determining the concentration of the at least one gas in the sample gas by detecting a phase difference between the first and second recombined signals.

23. The method of claim 22, further comprising modulating a phase of the first or second recombined signal by changing a path length of the second beam of radiation along the reference path using one or more retro-reflectors.

24. The method of claim 16, further comprising:
splitting, by a beam splitter, the extracted beam of radiation into the first beam, the second beam, a third beam and a fourth beam of radiation;
directing the second and fourth beams of radiation through a reference path containing a reference gas;
directing the third beam of radiation toward a first mirror positioned at an input of the sample cell, wherein the third beam of radiation is substantially reflected by the first mirror toward the beam splitter;
directing the second beam of radiation through the sample cell toward a second mirror positioned at an output of the sample cell, wherein the second beam of radiation is substantially reflected by the second mirror through the sample cell toward the beam splitter;
combining the first and second beams of radiation at the beam splitter to generate the first recombined beam of radiation; and
combining the fourth and third beams of radiation at the beam splitter to generate the second recombined beam of radiation.

25. The method of claim 24, further comprising:
receiving, by a third mirror, the first and second recombined beams of radiation;
directing, by the third mirror, the first recombined beam of radiation to a first detector to generate a first recombined signal; and
directing, by the third mirror, the second recombined beam of radiation to a second detector to generate a second recombined signal.

26. The method of claim 25, further comprising determining the concentration of the at least one gas in the sample gas by computing a phase difference between the first and second recombined signals.

* * * * *